United States Patent [19]
Plasterk et al.

[11] Patent Number: 6,051,430
[45] Date of Patent: Apr. 18, 2000

[54] VECTORS AND METHODS FOR PROVIDING CELLS WITH ADDITIONAL NUCLEIC ACID MATERIAL INTEGRATED IN THE GENOME OF SAID CELLS

[75] Inventors: Ronald Hans Anton Plasterk, Bussum; Domenico Valerio; Govert Johan Schouten, both of Leiden; Hendricus Gerhard Adrianus Maria van Luenen; Jan C. Vos, both of Amsterdam, all of Netherlands

[73] Assignees: Het Nederlands Kanker Instituut, Amsterdam; IntroGene B.V., Leiden, both of Netherlands

[21] Appl. No.: 09/317,062

[22] Filed: May 7, 1999

Related U.S. Application Data

[63] Continuation of application No. 08/909,786, Aug. 12, 1997, and a continuation-in-part of application No. PCT/NL97/00040, Feb. 7, 1997.

[30] Foreign Application Priority Data

Sep. 2, 1996 [EP] European Pat. Off. .............. 96200298

[51] Int. Cl.⁷ .............................. C12N 15/87; C12N 5/00; C07H 21/04
[52] U.S. Cl. ....................... 435/462; 435/320.1; 435/325; 536/23.1
[58] Field of Search ................................ 435/462, 320.1, 435/325; 536/23.1

[56] References Cited

U.S. PATENT DOCUMENTS

| | | | |
|---|---|---|---|
| 4,686,184 | 8/1987 | Puhler et al. | 435/6 |
| 4,830,965 | 5/1989 | Narang et al. | 435/473 |
| 5,348,874 | 9/1994 | Savakis et al. | 435/464 |
| 5,840,865 | 11/1998 | Savakis et al. | 536/23.2 |

FOREIGN PATENT DOCUMENTS

| | | |
|---|---|---|
| 0 485 701 A1 | 5/1992 | European Pat. Off. . |
| 96200298 | 2/1996 | European Pat. Off. . |
| WO 88/01646 | 3/1988 | WIPO . |
| WO 92/06205 | 4/1992 | WIPO . |
| WO 95/01095 | 1/1995 | WIPO . |
| PCT/NL97/ 00040 | 2/1997 | WIPO . |
| WO97/29202 | 8/1997 | WIPO . |

OTHER PUBLICATIONS

Bainton et al., "Tn7 Transposition In Vitro Proceeds through an Excised Transposon Intermediate Generated by Staggered Breaks in DNA," *Cell*, vol. 65, pp. 805–816, May 31, 1991.

Bainton et al., "Tn7 Transposition: Target DNA Recognition Is Mediated by Multiple Tn7–Encoded Proteins in a Purified In Vitro System," *Cell*, vol. 72, pp. 931–943, Mar. 26, 1993.

Beall et al., "A Drosophila protein homologous to the human p70 Ku autoimmune antigen interacts with the P transposable element inverted repeats," *Proc. Natl. Acad. Sci. USA*, vol. 91, pp. 12681–12685, Dec. 1994.

Bender et al., "Genetic Evidence That Tn 10 Transposes by a Nonreplicative Mechanism," *Cell*, vol. 45, pp. 801–815, Jun. 20, 1986.

Bolland et al., "The two single–strand cleavages at each end of Tn10 occur in a specific order during transposition," *Proc. Natl. Acad. Sci. USA*, vol. 92, pp. 7814–7818, Aug. 1995.

Boyd et al., "The pCLIP plasmids: versatile cloning vectors based on the bacteriophage λ origin of replication," *Gene*, 153, pp. 57–62, 1995.

Clark, James M., "Novel non–templated nucleotide addition reactions catalyzed by procaryotic and eucaryotic DNA polymerases," *Nucleic Acids Research*, vol. 16, No. 20, pp. 9677–9686, 1988.

Collins et al., "Activation of a transposable element in the germ line but not the soma of *Caenorhabditis elegans*," *Nature*, vol. 328, 20, pp. 726–728, Aug. 1987.

Colloms et al., "DNA binding activities of the Caenorhabditis", *Nucleic Acids Research*, vol. 22, No. 25, pp. 5548–5554, 1994.

Craxton, Molly, Linear Amplification Sequencing, a Powerful Method for Sequecing DNA, *METHODS: A Companion to Methods in Enzymology*, vol. 3, No. 1, pp. 20–26, Aug. 1991.

Doak et al., "A proposed superfamily of transposase genes: Transposon–like elements in ciliated protozoa and a common "D35E" motif," *Proc Natl. Acad. Sci. USA*, vol. 91, pp. 942–946, Feb. 1994.

Emmons et al., "Evidence for a Transposon in *Caenorhabditis elegans*," *Cell*, vol. 32, pp. 55–65, Jan. 1983.

Fallaux et al., "Characterization of 911: A New Helper Cell Line for the Titration and Propagation of Early Region 1–Deleted Adenoviral Vectors," *Human Gene Therapy*, vol. 7 pp. 215–222, Jan. 20, 1996.

Flinn et al., "Use of Gene Replacement to Construct *Escherichia coli* Strains Carrying Mutations in Two Genes Required for Stability of Multicopy Plasmids," *Journal of Bacteriology*, vol. 171, No. 4, pp. 2241–2243, Apr. 1989.

(List continued on next page.)

*Primary Examiner*—John S. Brusca
*Assistant Examiner*—William Sandals
*Attorney, Agent, or Firm*—Trask, Britt & Rossa

[57] ABSTRACT

The present invention provides novel elements for improving genetic engineering techniques for producing recombinant nucleic acid molecules and/or recombinant cells. The novel elements are capable of integrating desired nucleic acid material into other nucleic acid materials, specifically into the genome of a host cell. The novel elements are derived from or based on transposons, in particular from the Tc/Mariner superfamily. In particular, the essential elements of Tc1 enabling excision and pasting of the desired nucleic acid material are provided, together with the relevant transposase activity in cis or in trans.

19 Claims, 9 Drawing Sheets

OTHER PUBLICATIONS

Grindley et al., "Sequence Analysis at IS1 Insertion Sites: Models for Transposition," ENDFIELD *Cold Spring Harbor Symp. Quant. Biol.*, 45, pp. 1257–1261.

Grosschedl et al., HMG domain proteins: architectural elements in the assembly of nucleoprotein structures, *TIG*, vol. 10, No. 3, pp. 94–100, Mar. 1994.

Gunzburg et al., "Virus vector design in gene therapy", *Molecular Medicine Today*, vol. 1(9), pp. 410–417, 1995.

Henikoff, Steven, "Detention of Caenorhabditis Transposon Homologs in Diverse Organisms," *The New Biologist*, vol. 4, No. 4, pp. 382–388, Apr. 1992.

Kaufman et al., "P Element Transposition In Vitro Proceeds by a Cut–and–Paste Mechanism and Uses GTP as a Cofactor," *Cell*, vol. 69, pp. 27–39, Apr. 3, 1992.

Kramer et al., "The *Caenorhabditis elegans rol–6* Gene, Which Interacts with the sqt–1 Collagen Gene To Determine Organismal Morphology, Encodes a Collagen," *Molecular and Cellular Biology*, vol. 10., No. 5, pp.2081–2089, May 1990.

Loukeris et al., "Gene Transfer into the Medfly, *Ceratitis Capitata*, with a *Drosophila hydei* Transposable Element," Science, vol. 270, pp. 2002–2005, Dec. 22, 1995.

Mello et al., "Efficient gene transfer in C.elegans: extrachromosomal maintenance and integration of transforming sequences," *The EMBO Journal*, vol. 10, No. 12, pp. 3959–3970, 1991.

Mizuuchi, Kiyoshi, "Transpositional Recombination: Mechanistic Insights from Studies of Mu and Other Elements," *Annu. Rev. Biochem.*, vol. 61, pp. 1011–1051, 1992.

Müller et al., "DNA bending creates favored sites for retroviral integration: an explanation for perferred insertion sites in nucleosomes," *The EMBO Journal*, vol. 13, No. 19, pp. 4704–4714, 1994.

Nagai et al., "Synthesis and Sequence–Specific Proteolysis of Hybrid Proteins Produced in *Escherichia coli*," *Methods Enzymol.*, 153, pp. 461–481.

Paull et al., "The nonspecific DNA–binding and –bending proteins HMG1 and HMG2 promote the assembly of complex nucleoprotein structures," *Genes & Development*, vol. 7, pp. 1521–1534, 1993.

Plasterk, Ronald H.A., "The origin of footprints of the Tc1 transposon of *Caenorhabditis elegans*," *The EMBO Journal*, vol. 10, No. 7, pp. 1919–1925, 1991.

Plasterk, Ronald H.A., "Transposable Elements," Current Topics in Microbiology and Immunology, vol. 204, pp. 125–143, 1996.

Pryciak, Peter M., "Nucleosomes, DNA–Binding Proteins, and DNA Sequence Modulate Rettoviral Integration Target Site Selection," *Cell*, vol. 69, pp. 769–780. May 29, 1992.

Radice et al., "Widespread occurrence of the Tc1 transposon family: Tc1 –like transposons from teleost fish," *Mol Gen Genet*, vol. 244, pp. 606–612, 1994.

Rio et al., "Evidence for Drosophila P Element Transposase Activity in Mannalian Cells and Yeast," *J. Mol. Biol.*, vol. 200, pp. 411–415, 1988.

Robertson, Hugh M., "The Tc1 –mariner Superfamily of Transposons in Animals," *J. Insect Physiol.*, vol. 41, No. 2, pp. 99–105, 1995.

Robertson, Hugh M., "The mariner transposable element is widespread in insects," *Natur*, vol. 362, pp. 241–245, Mar. 18, 1993.

Robertson et al., "Recent Horizontal Transfer of a mariner Transposable Element among and between Diptera and Neuroptera," *Mol. Biol. Evol.*, vol. 12(5), pp. 850–862, 1995.

Schukkink et al., "TcA, the putative transposase of the C. elegans Tc1 transposon, has an N–terminal DNA binding domain," *Nucleic Acids Research*, vol. 18, No. 4, pp. 895–900. 1990.

Shapiro, James a., "Molecular model for the transposition and replication of bacteriophage Mu and other transposable elements," *Proc. Natl. Acad, Sci. USA*, vol. 76, No. 4, pp. 1933–1937, Apr. 1979.

van Luenen et al., "Target site choice of the related transposable elements Tc1 and Tc3 of *Caenorhabditis elegans*," *Nucleic Acids Research*, vol. 22, No. 3, pp. 262–269, 1994.

Vos et al., "Characterization of the *Caenorhabditis elegans* Tc1 transposase in vivo and in vitro," *Genes & Development*, vol. 7, pp. 1244–1253, 1993.

Vos et al., "Tc1 transposase of *Caenorhabditis elegans* is a endonuclease with a bipartite DNA binding domain," *The EMBO Journal*, vol. 13, No. 24, pp. 6125–6132, 1994.

Vos et al., "Transposase is the only nematode protein required for in vitro transposition of Tc1", *Genes & Development*, 10:755–761 (1996).

Way et al., "The mec–3 gene contains cis–acting elements mediating positive and negative regulation in cells produced by asymmetric cell division in *Caenorhabditis elegans*," *Genes & Development*, vol. 5, pp. 2199–2211, 1991.

Zabarovsky et al., "High efficiency electroporation of ligated DNA into bacteria," *Nucleic Acids Research*, vol. 18, No. 19, p. 5912, 1990.

SEQUENCE LISTING

<160> NUMBER OF SEQ ID NOS: 10

<210> SEQ ID NO 1
<211> LENGTH: 44
<212> TYPE: DNA
<213> ORGANISM: Plasmid pRc/CMV.Tc1A

<400> SEQUENCE: 1
ccccaagctt gccaccatgg taaaatctgt tgggtgtaaa aatc            44

<210> SEQ ID NO 2
<211> LENGTH: 32
<212> TYPE: DNA
<213> ORGANISM: Plasmid pRc/CMV.Tc1A

<400> SEQUENCE: 2
gctctagatg cttaatactt tgtcgcgtat cc                         32

<210> SEQ ID NO 3
<211> LENGTH: 56
<212> TYPE: DNA
<213> ORGANISM: Artificial Sequence
<220> FEATURE:
<223> OTHER INFORMATION: Description of Artificial Sequence: vectorette
      oligonucleotide 503 ligated to digested genomic
      fragments to facilitate sequencing of DNA flanking
      integrated transposon

<400> SEQUENCE: 3
gatccaagga gaggacgctg tctgtcgaag gtaaggaacg gacgagagaa gggaga    56

<210> SEQ ID NO 4
<211> LENGTH: 52
<212> TYPE: DNA

-continued

```
<213> ORGANISM: Artificial Sequence
<220> FEATURE:
<223> OTHER INFORMATION: Description of Artificial Sequence: vectorette
      oligonucleotide 504 ligated to digested genomic
      fragments to facilitate sequencing of DNA flanking
      integrated transposon

<400> SEQUENCE: 4
tctcccttct cgaatcgtaa ccgttcgtac gagaatcgct gtcctctcct tg          52

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: vectorette
      oligonucleotide Tc1L2 ligated to digested genomic
      fragments to facilitate sequencing DNA flanking
      integrated transposon

<400> SEQUENCE: 5
tcaagtcaaa tggatgcttg ag                                           22

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: vectorette
      oligonucleotide Tc1R2 ligated to digested genomic
      fragments to facilitate sequencing DNA flanking
      integrated transposon

<400> SEQUENCE: 6
gattttgtga acactgtggt gaag                                         24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: vectorette
      oligonucleotide 337new ligated to digested genomic
      fragments to facilitate sequencing DNA flanking
      integrated transposon

<400> SEQUENCE: 7
gtacgagaat cgctgtcctc                                              20

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: sequence
      primer

<400> SEQUENCE: 8
agatttccac ttatatcatg ttttatgttt tgc                               33

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence:
      oligonucleotide used to determine the positions of
      double stranded cleavages at the nucleotide level
```

-continued

```
<400> SEQUENCE: 9
ctctgctcat atgtcacgac cggtttttct ataggtg                              37

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence:
      oligonucleotide used to determine the positions of
      double stranded cleavages at the nucleotide level

<400> SEQUENCE: 10
cacctataga aaaaccggtc gtgacatatg agcagag                              37
```

VECTORS AND METHODS FOR PROVIDING CELLS WITH ADDITIONAL NUCLEIC ACID MATERIAL INTEGRATED IN THE GENOME OF SAID CELLS

CROSS REFERENCE TO RELATED APPLICATION

This application is a continuation of application Ser. No. 08/909,786, filed Aug. 12, 1997, pending, the contents of which are incorporated by this reference which claims priority from, and is a continuation-in-part, of International Application No. PCT/NL97/00040, filed on Feb. 7, 1997 designating the United States of America.

TECHNICAL FIELD

The present invention relates generally to the field of genetic engineering, in particular to methods of making recombinant vectors containing nucleic acids of interest, methods for making recombinant cells, preferably expressing recombinant products, and/or production of nucleic acids of interest.

The invention also relates to transgenesis of animals, plants or other organisms of medical, scientific or economic interest. The invention also relates to tools for mutagenesis as well as to tools and means for localization and/or identification of nucleic acid sequences of interest (such as genes) in the genome of a host.

BACKGROUND

Many ways of providing cells with additional nucleic acids are now known in the field. Many proteins have been expressed in many kinds of cells, ranging fro prokaryotic bacteria and bacilli, via yeast and fungi, to plant cells, insect cells and mammalian cells.

Often, expression of proteins as previously discussed has met with success. There are, however, certain areas in the field of recombinant technology where, because of safety issues or technical problems, such as stability of the additional nucleic acid material introduced, success has not been easy to achieve. Also, in the application of genetic engineering where the product is not a protein but, for instance, a nucleic acid of interest (such as DNA, RNA or an antisense construct), the same or similar problems have been encountered. It is in these areas particularly that the present invention finds its particular use.

One of the problems encountered in recombinant technology is that it is often desirable to have the additional nucleic acid material, which is introduced into a host cell, integrate into the genome of the host cell. Once the additional nucleic acid material is integrated in the genome, its stability is much less an issue. Moreover, the integrated material is replicated together with the genome and thus will be present in the offspring of the recombinant cell as well. Vectors which are capable of providing for integration of additional nucleic acid material into a host cell are known, but they suffer from some drawbacks which will be discussed herein.

One of the drawbacks of the integrating vectors of the prior art is that they are often not capable of transducing a host cell efficiently. Techniques such as electroporation and the like are then necessary for achieving transduction.

In some areas, such treatments of cells may be unwanted or impossible. One such an area is, for instance, gene therapy. In such cases, vectors which can efficiently transduce host cells on their own, or which can be packaged into recombinant viral particles and so infect host cells, are often employed. However, many of these vectors are then incapable of efficient integration of the desired additional nucleic acid material in the genome of the host.

SUMMARY OF THE INVENTION

The present invention now provides a way in which a wide variety of vectors can be altered to integrate the desired additional nucleic acid in the genome of the host cell. This means that vectors which did not (efficiently) integrate the desired additional nucleic acid material in the genome of the host cell can now be provided with the ability.

The present invention offers the best of both worlds in that it enables preparation of vectors capable of efficiently transducing and efficiently integrating desired additional nucleic acid material into a host cell. The invention solves this problem in that the nucleic acid to be integrated into a host cell genome is provided within a functional transposon. Exogenous DNA has been introduced into the genome of a host using a transposon; however, since transposons were, until the present invention, thought to be rather species specific, the applicability of such a system was thought to be very limited. At best, it was shown that a transposon functional in one fruit fly could also be used to integrate DNA into the genome of another species of fruit fly (Loutheris et al., 1995). The present inventors have found that, at least for a certain class of transposons, it is possible to use these transposons across wide phylogenetic barriers, which allows for wide application of these transposons as integrations means for DNA into a wide variety of host genomes.

The invention thus provides a vector for providing a cell of a certain genus with additional nucleic acid material integrated in its genome, whereby the vector comprises two transposase binding sites, whereby the transposase binding sites may be the same or different and are derived from a transposon found in another genus, each in close proximity to a cut site for the transposase, whereby the additional nucleic acid material is located between the two transposase binding sites. It is, of course, clear that it is highly preferred to be able to use transposons over even wider phylogenetic barriers. The present invention thus provides a transposon-based integration system with a wide applicability.

Clear advantages of this system are, for instance, that using a transposon will often lead to a more efficient integration into the host cell genome. Using a transposon gives complete control of the integrating sequence (the termini of the integrating element are known). In the embodiment where gene (or DNA) localization is desired, it will be an advantage that a transposon can integrate anywhere in the genome (especially useful in so-called mutagenesis experiments aimed at gene function, or in "gene-trap" experiments directed at tracing genes of interesting expression patterns). For expression purposes, it may be desirable to develop transposons with a more specific integration site in the genome, or to develop methods of integration which lead to a more specific integration site.

Preferably, the transposase binding sites and cut sites are based on the corresponding sites in transposon s from the Tc1/mariner superfamily of transposons; more preferably, they are based on Tc1-like transposons. A very useful set of transposon elements in the minimum set required by the Tc1 transposon i.e., comprising the terminal 26 basepairs of Tc1 and in close proximity the cut site (TA) for Tc1 transposase.

An important advantage of the transposons according to the invention is that they are self-sufficient. All that is needed is a functional transposase binding site, a transposase cut site, and transposase activity functional for those sites. Transposase activity needed should be as limited as possible. The preferred class of transposons only needs a single transposase. A reason for the species-specificity of transposons reported to date may be that transposons have been used that require host proteins in order to be able to jump. The host proteins may then be responsible for the species-specificity of, for instance, the transposons of bacterial origin, or the P-element. The class provided with the present invention needs no host-elements and has modes cis-trans requirements. Therefore, these transposons are far more suitable for integrating nucleic acids of interest into the genome of a wide variety of hosts.

In the preferred embodiment where elements based on Tc1 are used, such a transposon binding site seems to be at least the 26 terminal basepairs ("bp"). Probably not all of these basepairs are essential for the function of this binding site. Some (conservative) changes in such a binding site may therefore be allowed. It seems that sequences of around 100 bp are most efficient as transposase recognition sites.

For the invention, they are functional for the corresponding transposase-activity, which transposase, of course, may also be modified, mutated, shortened or lengthened when compared with the original transposase, as long as it has relevant transposase-activity. The transposase-activity may be encoded on the same vector as the other transposon elements, even as part of the transposon together with the desired additional nucleic acid material (in cis), but it may very suitably be provided to the cell to be transduced by another vector according to the invention or by another vector (in trans).

When the transposase-activity is provided in trans and is preferably encoded by a sequence under control of an inducible and/or repressible promoter, "jumping" of the transposon can be switched on and off. Once integration into the host genome has taken place, this may be very useful.

A vector for the purposes of this invention is any nucleic acid vehicle which is capable of carrying the desired additional nucleic acid material and preferably capable of transduction of host cells and/or replication.

The desired additional nucleic acid material may encode a protein and thus include a gene and regulatory elements for expression. Proteins to be expressed will depend on the purpose of the transduction. Many useful proteins for any applications have been identified as good candidates for recombinant expression. All these may be expressed using the present invention.

Also, the additional nucleic acid material (DNA) may be transcribed (once transduced) into RNA molecules blocking transcription or translation of host cell (or viral) nucleic acids. Such additional nucleic acid material may, for instance, be an antisense RNA molecule.

Use of the invention in the field of gene therapy may be particularly advantageous. Viral vectors often contemplated for gene therapy (such as adenovirus, retrovirus or adenoassociated virus) which are not capable of efficiently integrating the desired nucleic acid material into the genome of the infected cell may now be provided with such capability. Other vectors not based on a virus, but provided with a means to deliver them to a target cell population, can, of course, also be advantageously provided with an integration system according to the invention. Particularly, the use of liposomes or polymers as a targeting system is contemplated.

As stated earlier, the cell's progeny will also have that capability. Thus, when stemcells are produced according to the invention, this will lead to very efficient gene therapy regimes. The vectors (or the integration system) of the invention can, of course, also be used to produce transgenic animals, plants or other organism of scientific, economic or medical interest. Useful applications for transgenesis are well known in the art.

Thus, methods using the vectors according to the invention to transduce cells or animals, plants, etc. are also disclosed and part of the invention, as are cells, animals or plants, etc. obtainable by such methods. Use of the invention in mutagenesis studies and the like is another preferred embodiment, as discussed hereinbefore. The invention will now be explained in more detail using Tc1 as a non-limitative example.

DETAILED DESCRIPTION OF THE INVENTION

Tc1 belongs to the Tc1/mariner superfamily of transposons found in nematodes, arthropods and chordates (Henikoff 1992; Raddice et al. 1994; Robertson 1995; Plasterk 1995). Both vertical and horizontal transfer have contributed to the spread of these elements throughout the animal kingdom (Robertson 1993; Radice et al. 1994; Robertson and Lampe 1995). The widespread occurrence of the Tc1/mariner family of transposons can be taken as an indication for the absence of species-specific host factors which limit the transfer between different species. Therefore, Tc1/mariner elements are attractive candidates for the development of gene delivery vectors.

Tc1-like elements are close to 1.7 kb in length, have short inverted terminal repeats (ITR's) flanking a transposase gene and have the conserved sequence CAGT at their termini, flanked by TA representing the target site, which is duplicated upon integration (Van Luenen et al. 1994). The element-encoded proteins share a homologous catalytic domain with bacterial transposases and retroviral integrases (Doak et al. 1994). Tc1 from *C. elegans* is a 1612 bp long transposon which has 54 bp inverted repeats flanking a gene encoding a 343 amino acid transposase (Enunons et al. 1983; Rosenzweig et al. 1983; Vos et al. 1993), that binds to the inverted repeats (Vos et al. 1993; Vos and Plasterk 1994). The conserved hexanucleotide sequence, TACAGT, at the extreme termini of the element is not part of the transposase binding site, but is thought to play a role in catalysis of the transposition reaction (Vos and Plasterk 1994).

Here, we describe in vitro excision and transposition of Tc1 using an extract prepared from transgenic nematodes. The minimal cis-requirements for transposition are defined and the target site choice in vitro is compared with that in vivo. Furthermore, we demonstrate that recombinant transposase purified from *E. coli* is capable of supporting transposition, showing that no other factors are essential for Tc1 transposition in vitro.

Moreover, we show that Tc1-transposase supports jumping of Tc1-derived transposons carrying a neomycin resistance gene into the genome of human cells. This demonstrates that is possible to construct transposon-derived vectors that are capable of providing for integration of additional nucleic acid material into host cells across large phylogenetic barriers, which makes such vectors suitable as integrating gene delivery vehicles for a wide variety of host genomes, including that of humans.

RESULTS

Transposition of Tc1 In Vitro

Figure 1:
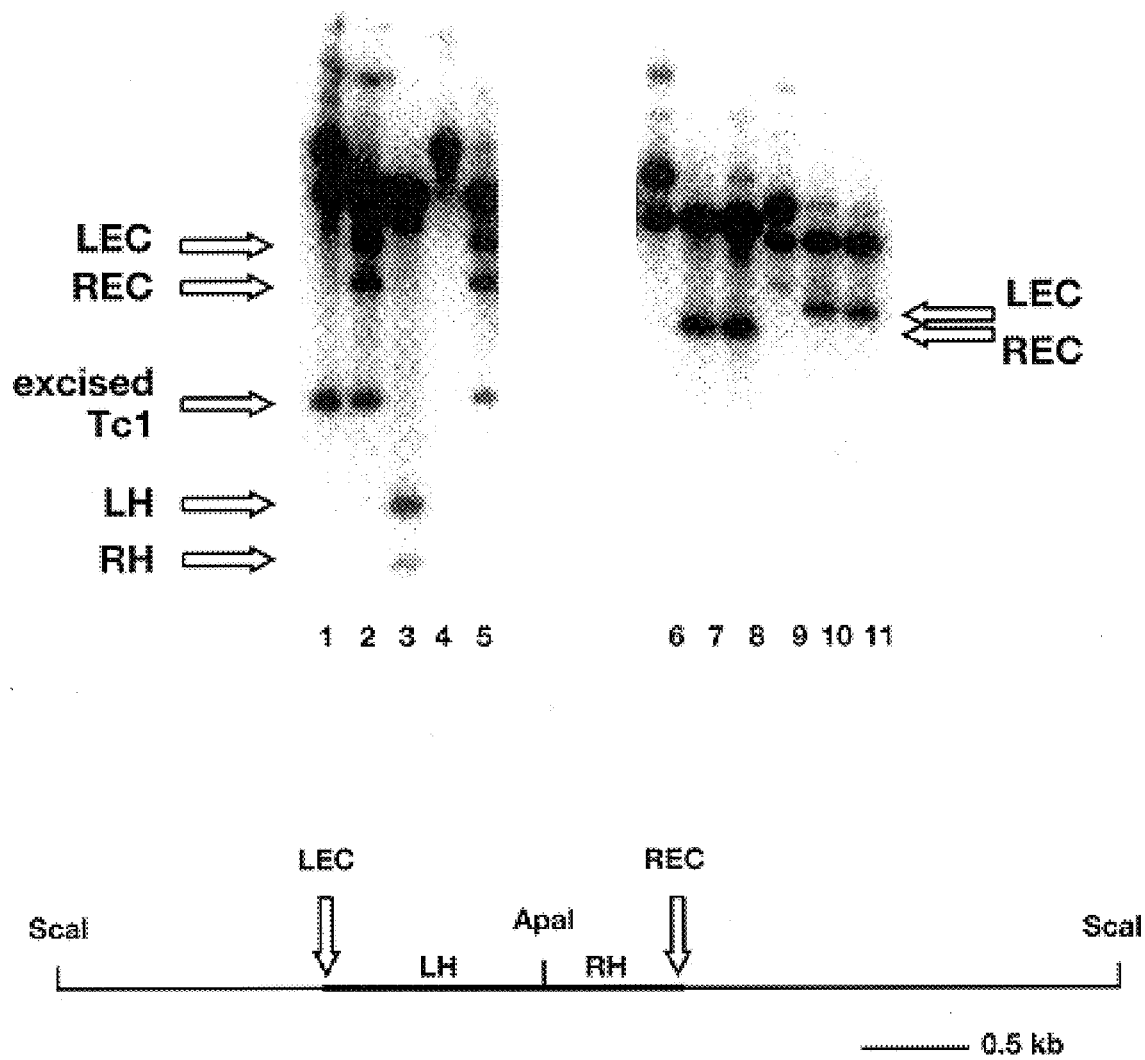
FIG. 1 is a Southern Blot analysis of in vitro Tc1 transposition reaction products. Products of in vitro transposition reactions were separated on a 1% agarose gel, transferred to nitrocellulose and probed with radiolabeled Tc1. Standard reactions contained $Mgcl_2$ (lanes 1–3 and 5–11) or EDTA (lane 4). Products were digested with ScaI in vector DNA (lane 2, 7, 10) or ApaI in Tc1 DNA (lane 3) prior to electrophoresis. Lanes 5, 8 and 11 show reaction products when the substrate is linearized with ScaI prior to in vitro cleavage. Lanes 1–5 show reaction products using pRP466 as substrate which carries a complete Tc1 element (see FIG. 4). Lanes 6–8 use pRP467 as substrate which has a deleted left end of Tc1, whereas Lanes 9–11 show pRP4678 as substrate, which has the right end of Tc1 deleted. REC and LEC stands for Right and Left End Cleavage, respectively. RH and LH indicate the positions of the Right and Left Half of Tc1. A schematic of ScaI-linearized pRP466 is shown at the bottom of the figure.

We generated a transgenic worm with the Tc1 transposase gene under the control of a heat shock promoter. This allowed the preparation of a nuclear extract with elevated levels of transposase, which proved to be highly important to detect activity. The extract was incubated with a plasmid containing a Tc1 element. Excision was studied in a physical assay. Southern Blot analysis of reaction products shows the appearance of excised Tc1 elements (FIG. 1, lane 1).

Furthermore, cleavage at either the left or the right end of Tc1 is detected when the products are digested with ScaI within the plasmid backbone prior to electrophoresis (lane 2). Cleavage may require a divalent cation ($Mg^{2+}$ or $Mn^{2+}$) and is stimulated by the presence of ethylene glycol or 5% DMSO (data not shown). The efficiency of cleavage at a single end of the transposon is not decreased if the substrate is linear (compare lanes 2 and 5). Also, deletion of either end of the transposon does not abolish cleavage at the remaining end (lanes 6 and 11), which suggests that cleavage does not require interaction between the two ends. In contrast to single end cleavage, excision of the complete element is reduced about 2-fold when the substrate is linear, suggesting that coordinated cutting at both ends is stimulated by supercoiling of the substrate. The majority of complete excision products observed with a linear substrate can be explained by non-coordinated cleavages at both ends.

Figure 2:
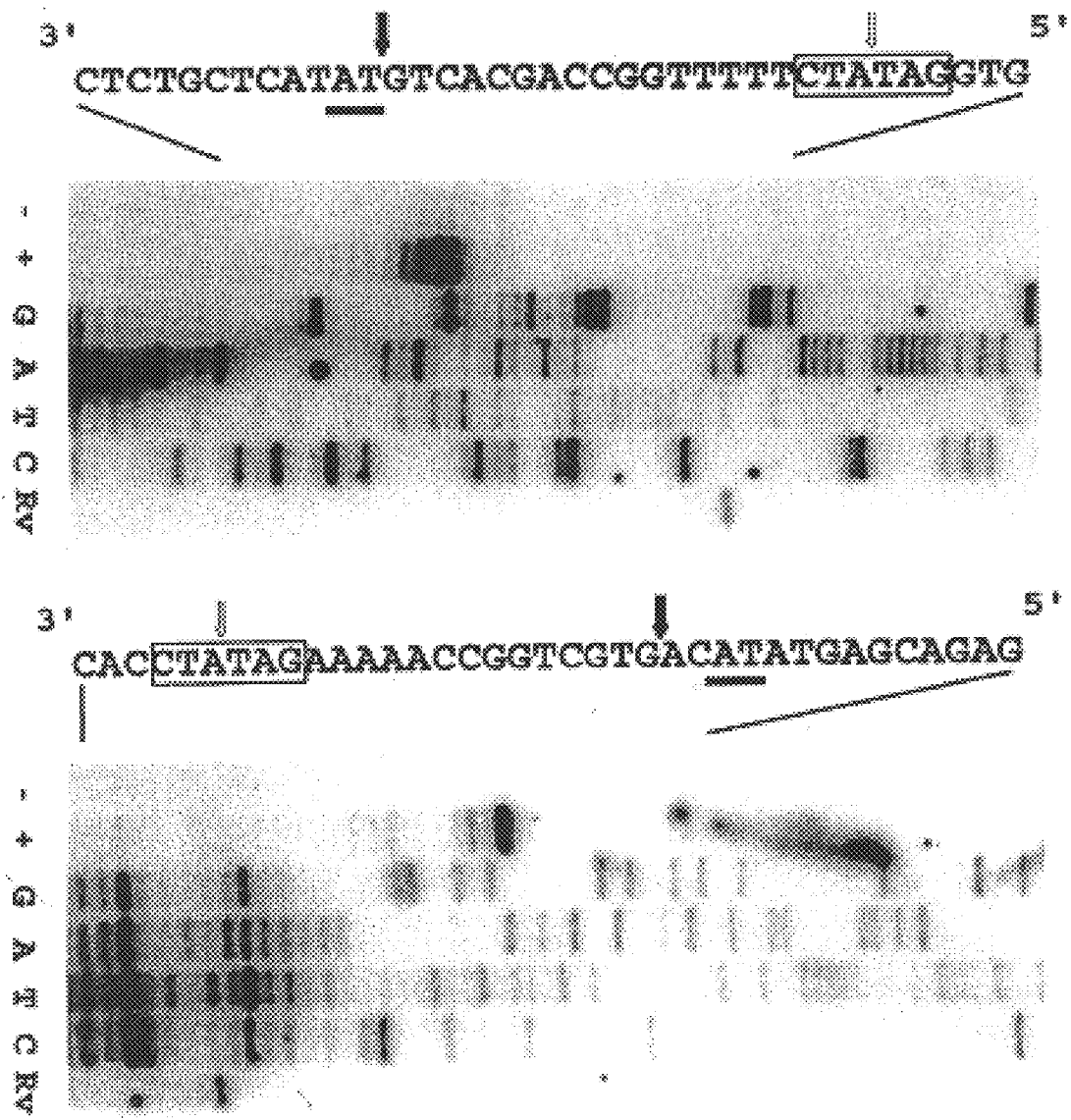
FIG. 2 is a mapping of the in vitro cleavage sites at the nucleotide level. A PCR based primer extension was performed on reaction products obtained in the presence of $Mgcl_2$ (+) or EDTRA (−) using pRP466 as donor. A control reaction was performed with pRP466 digested with EcoRV (RV lanes) to demonstrate the addition of one extra nucleotide at the end of the PCR product by Taq polymerase (see Clark 1988). Products were analyzed on a sequencing gel. Sequence reactions (GATC) were loaded as markers. PCR was with primer R2 (right panel) or primer BIGR (left panel). The relevant sequence is indicated with the EcoRV site boxed and the TA target site underlined. The cleavage sites are shown by arrows. Identical results were obtained when the positions of cleavage at the other transposon end were determined.

To determine the positions of the double strand cleavages at the nucleotide level, a PCR based primer extension was performed using end-labeled oligonucleotides specific for each strand (FIG. 2). The 5' cut is 2 bp within the transposon, whereas the 3' cut maps to the end of the transposon, as based on the largest observed PCR product. This confirms the model base on in vivo studies of the related *C. elegans* transposon Tc3, for which it was shown that excision results in a 2 bp staggered 3' overhang (Van Luenen et al. 1994). The complete excision of Tc1 shows that transposition occurs via a cut-and-paste process, a result consistent with genetic data on double strand break repair of the donor DNA molecule upon Tc1 excision (Plasterk 1991).

Figure 3:
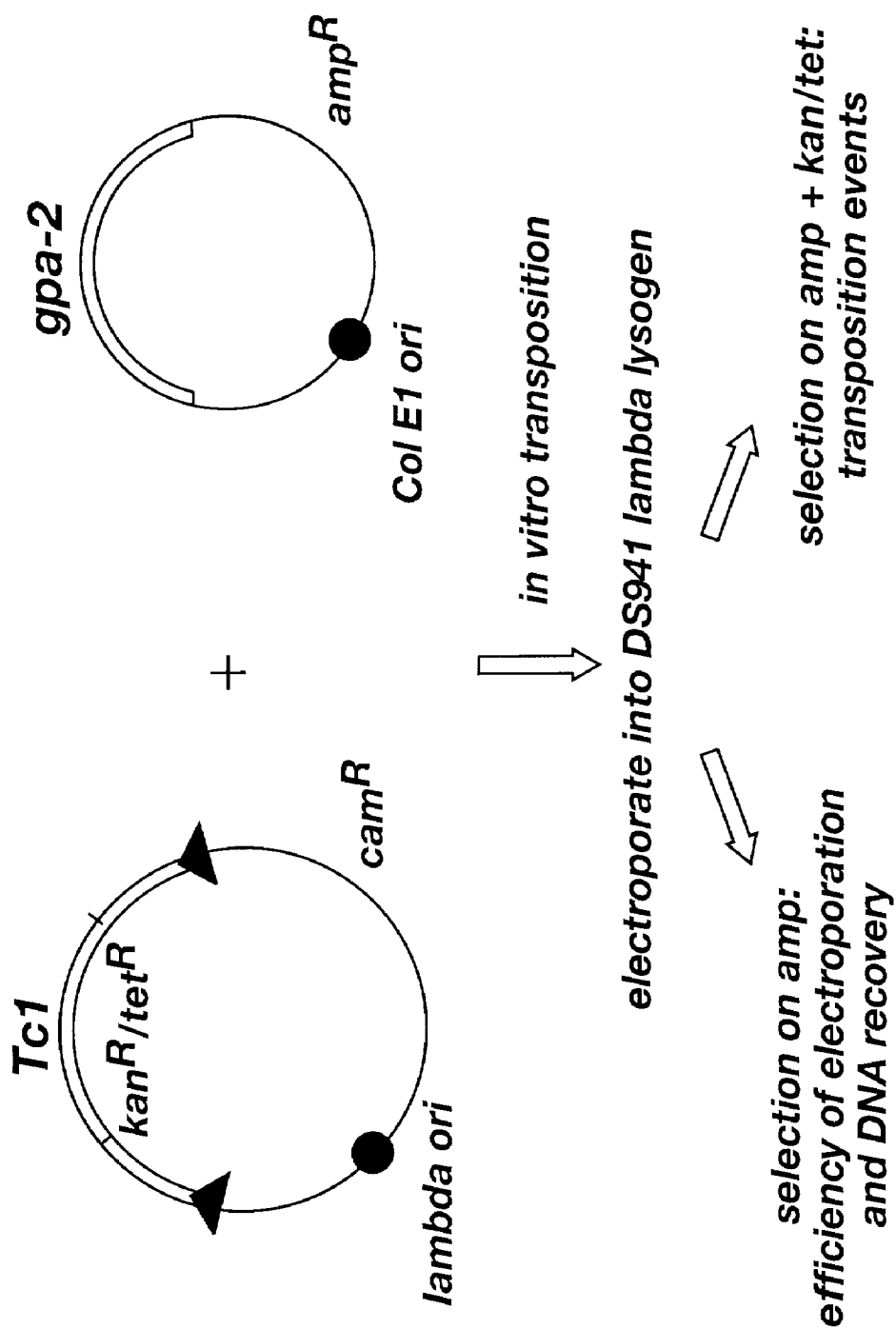
FIG. 3 is a schematic representation of the genetic transposition assay. The donor plasmid, a pACB104 derivative (Boyd and Sherratt 1995) with a lambda origin of replication, contains a Tc1 element carrying an antibiotic resistance gene. The target plasmid, pRP475, carries a 1,4 kb hindli gpa-2 fragment and a Col E1 origin of replication (pSP72, Promega). Reaction products were electroporated into a lambda lysogen E. coli strain to counterselect against the donor. Integration events were selected on double antibiotics.

We devised a sensitive assay to detect integration events. We selected for jumping of a transposon-borne antibiotic resistance gene from a supercoiled donor plasmid to a target plasmid in a genetic assay (FIG. 3). Electroporation of reaction products into the appropriate *E. coli* strain resulted in the detection of many transposition events (Table 1). Extracts prepared from non-transgenic N2 worms or from the so-called high-hopper strain, TR679 (Collins et al. 1987), which has a high frequency of germline transposition, do not generate a detectable level of transposition products in this assay. Linearization of the donor plasmid resulted in an approximately 20-fold reduced efficiency of transposition. Transposition requires two inverted repeat sequences, because no integrations were obtained upon deletion of one transposon end. Furthermore, the addition of ATP, GTP or dNTPs does not increase the level of transposition (data now shown), which indicates that the process is neutral in energy-consumption and independent of a cofactor. About 90 independent in vitro Tc1 integrations were analyzed by sequencing and found at TA dinucleotides, which had been duplicated in the process. Two odd integration events were detected, where Tc1 had integrated in the sequence TTG or CCT. In both cases, we found a 3 bp target site duplication.

Target Site Choice

Figure 4:
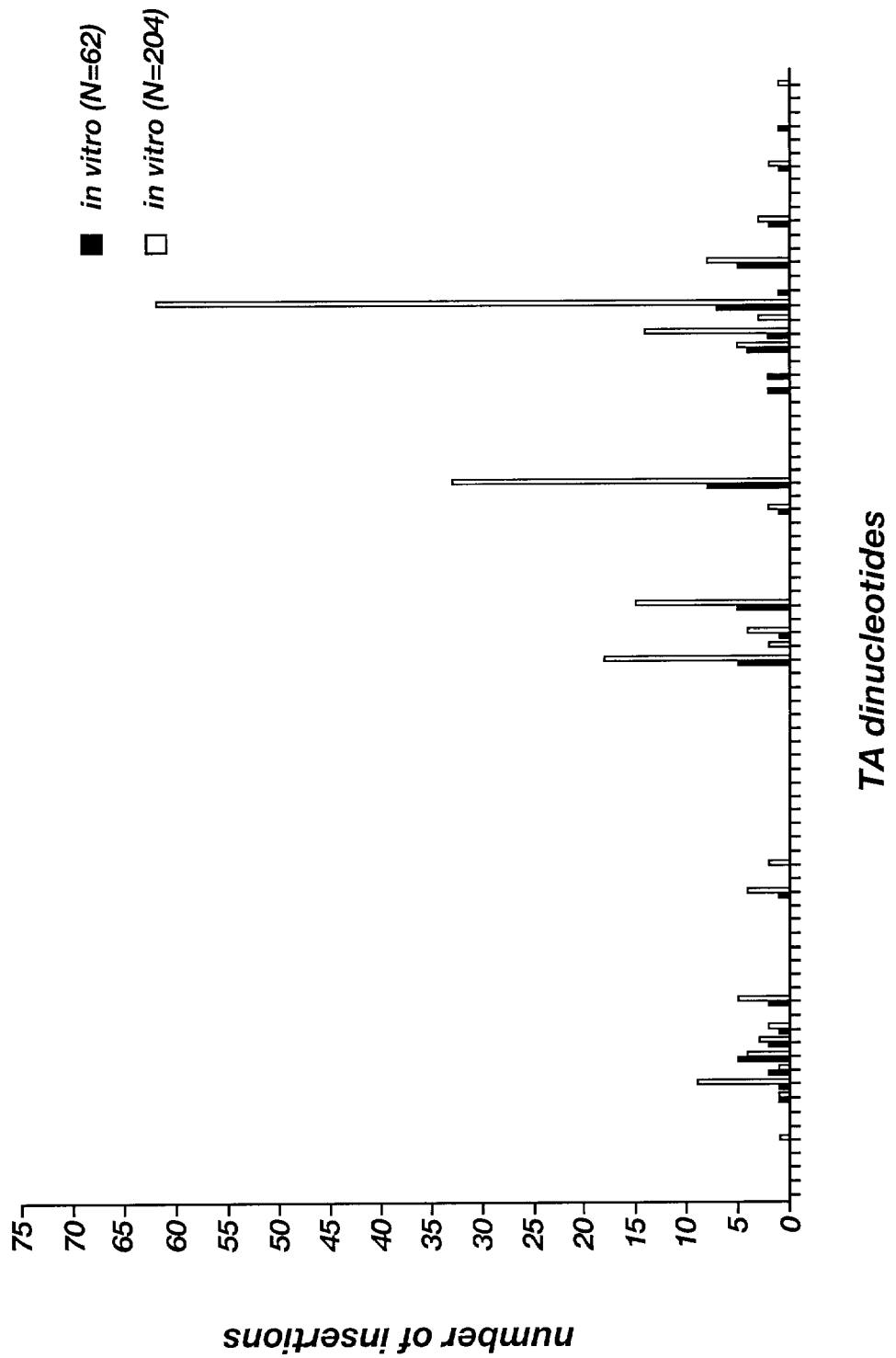
FIG. 4 depicts target site selection. Comparison of the distribution of in vitro (black bars) and in vivo (open bars) Tc1 insertions. pRP472 as donor and pRP475 as target were used in standard in vitro transposition reactions using C. elegans extract. Every mark on the X-axis represents a TA dinucleotide in the gpa-2 fragment as described in detail elsewhere (Van Luenen and Plasterk 1994).

Previously, several hundreds of in vivo Tc1 and Tc3 integrations in a 1 kb region of the gpa-2 gene have been analyzed (Van Luenen and Plasterk 1994). This showed the selective use of a limited set of TA dinucleotides as target-of integration, with a striking difference in preference between Tc1 and Tc3. To investigate whether the chromatin structure played a role in the choice of integration sites, we determined the pattern of integrations into naked DNA in vitro, using the same target region previously assayed in vivo. Therefore, we included the gpa-2 region in our target plasmid. It is apparent that the same overall pattern of integration is seen (FIG. 4). Hot sites in vivo appear to be hot in vitro and cold sites in vitro are also cold in vivo. This indicates that, at least in this region of the genome, the genome, the chromatin structure or the transcriptional status of the DNA in vivo is not the major determinant of target choice.

Transposition by Recombinant Transposase

Figure 5:
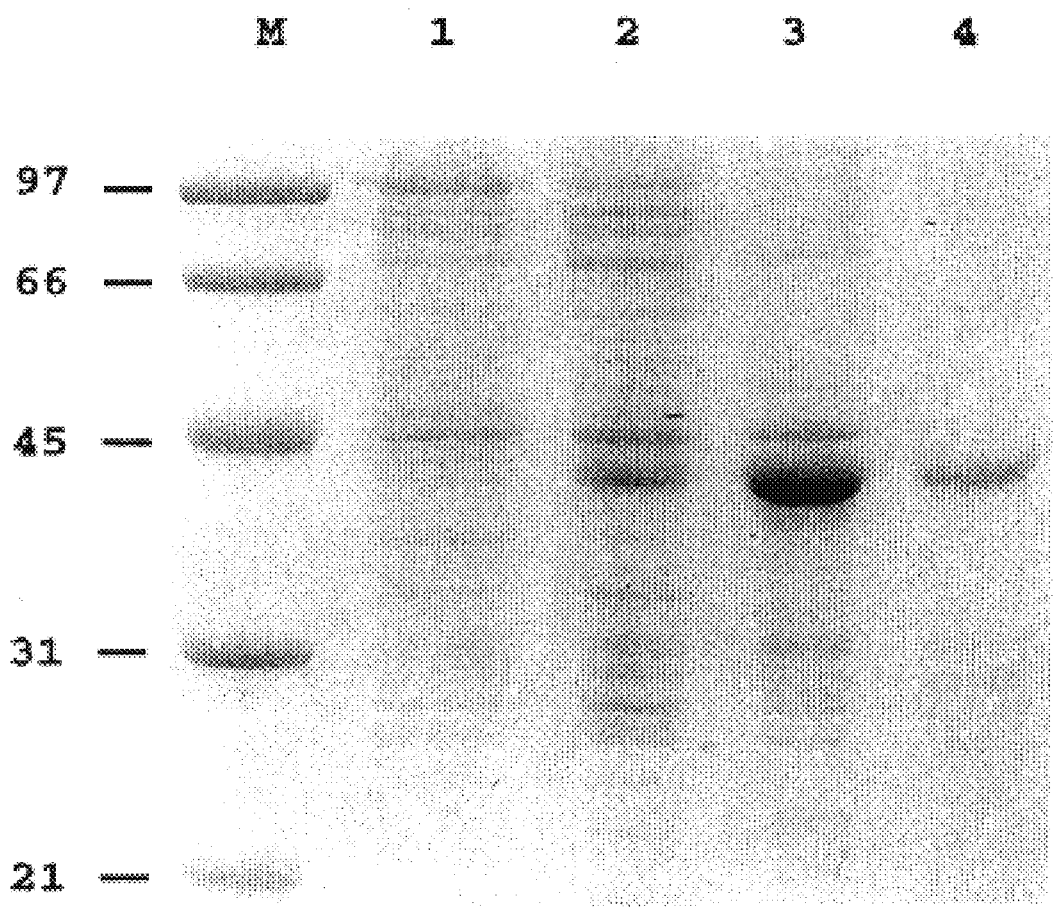
FIG. 5 depicts purification of Tc1 transposase from *E. coli*. Analysis of transposase purified from inclusion bodies on a 12% SDSi)olyacrylamide gel. Lane M: molecular weight markers (indicated in KDa); Lane 1: bacterial lysate before induction; Lane 2: bacterial lysate after induction; Lane 3: purified inclusion bodies; Lane 4: purified transposase after refolding.

The nematode is not a convenient source of protein for an extensive purification of a transposase. Therefore, we expressed the protein in a heterologous system. Both expression using Baculovirus and Sf9 cells (data not shown) or expression in *E. coli* yielded transposase capable of supporting Tc1 transposition. Recombinant transposase was purified from inclusion bodies to near homogeneity (FIG. 5). Table 1 shows the frequency of transposition when comparable amounts of transposase were used for both the worm extract and the purified protein. Sequence analysis of nine independent integrations in the case of the recombinant protein showed that transposition into TA target sequences that were duplicated, from which it can be concluded that bona fide transposition had occurred. Therefore, we conclude that Tc1 transposase is the only protein required for Tc1 transposition. The difference in efficiency between nematode derived and bacterial transposase needs further studies. It could reflect a folding problem of the bacterial transposase, which was denatured and refolded during the purification procedure, or the stimulatory role of host factors present in the nematode extract.

Minimal Cis-Requirements

We investigated the possibility that the terminal 26 bp of Tc1 which constitute a full transposase binding site, flanked by the TA target site, are sufficient to form an artificial transposon. An element consisting of only these Tc1-specific sequences is still able to transpose in vitro, albeit at a lower frequency (Table 1). We sequenced several integrations and found them to be correct.

TABLE 1: Transposition frequencies. In vitro Tc1 transposition reactions were carried out with supercoiled (SC) or linear donor plasmids and with protein sources as indicated and the ratios of $amp^R$-$kan^R$ to $amp^R$ colonies ($*10^6$) are shown for two independent experiments. No integration products were recovered when reactions were performed in the presence of EDTA.

TABLE 1

| Donor | source | exp. 1 | exp. 2 |
|---|---|---|---|
| pRP490, SC | C. elegans | 21.0 | 22.0 |
| pRP490, linear | C. elegans | 0.5 | 1.0 |
| pRP491, SC | C. elegans | 3.7 | 1.6 |
| pRP490, SC | E. coli | 3.0 | 3.2 |

Figure 6:
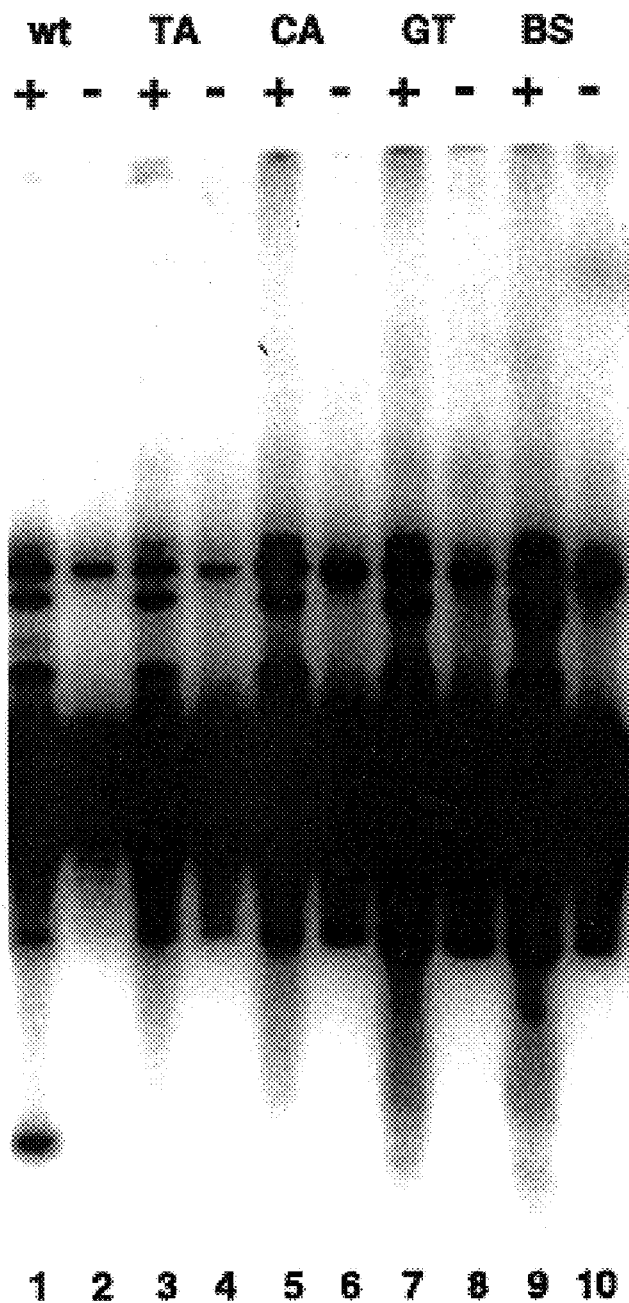
FIG. 6 shows that mutations at the extreme termini of Tc1 affect excision. In vitro reactions products were obtained using *C. elegans* extract in the presence of $Mgcl_2$ (+) or EDTE (−) using as donor pRP480 (wt), pRP481 (TA), pRP482 (CA), pRP483 (GT) or pRP484 (BS), as indicated at the top. Products were separated on a 1% agarose gel, transferred to nitrocellulose and probed with radiolabeled $Kan^R$-gene fragment. The donor plasmids contain 28-mers cloned into the SmaI-site (wt sequence) and the HindII-site (wt or mutant sequence) of pUC19 with the $Kan^R$-cassette of pUC4K in between. TA was mutated to CG, CA to TG and GT to AC, respectively. In the transposase binding site mutation the BalI and EcoRV sites were mutated to TCCCA and GGGCCC, respectively (see Vos and Plasterk 1994).

Furthermore, investigated the importance of the conserved hexanucleotide sequence TACAGT. Mutations were introduced at one of the ends of a mini-Tc1 which contains only the terminal 26 bp as well as the flanking TA dinucleotide. Whereas excision of the element with 2 wild-type ends is easily detected in a physical assay, mutation of the transposase binding site, the flanking TA sequence of the termini, resulted in the inability of the element to excise (FIG. 6). Double strand cleavage at the wild-type end was not affected by mutation at the other transposon end. Analysis of cleavage by PCR based primer extension revealed that, for the CA to TG mutation only, single stranded breaks at the 5' end of the transposon had occurred (data not shown).

Figure 7:
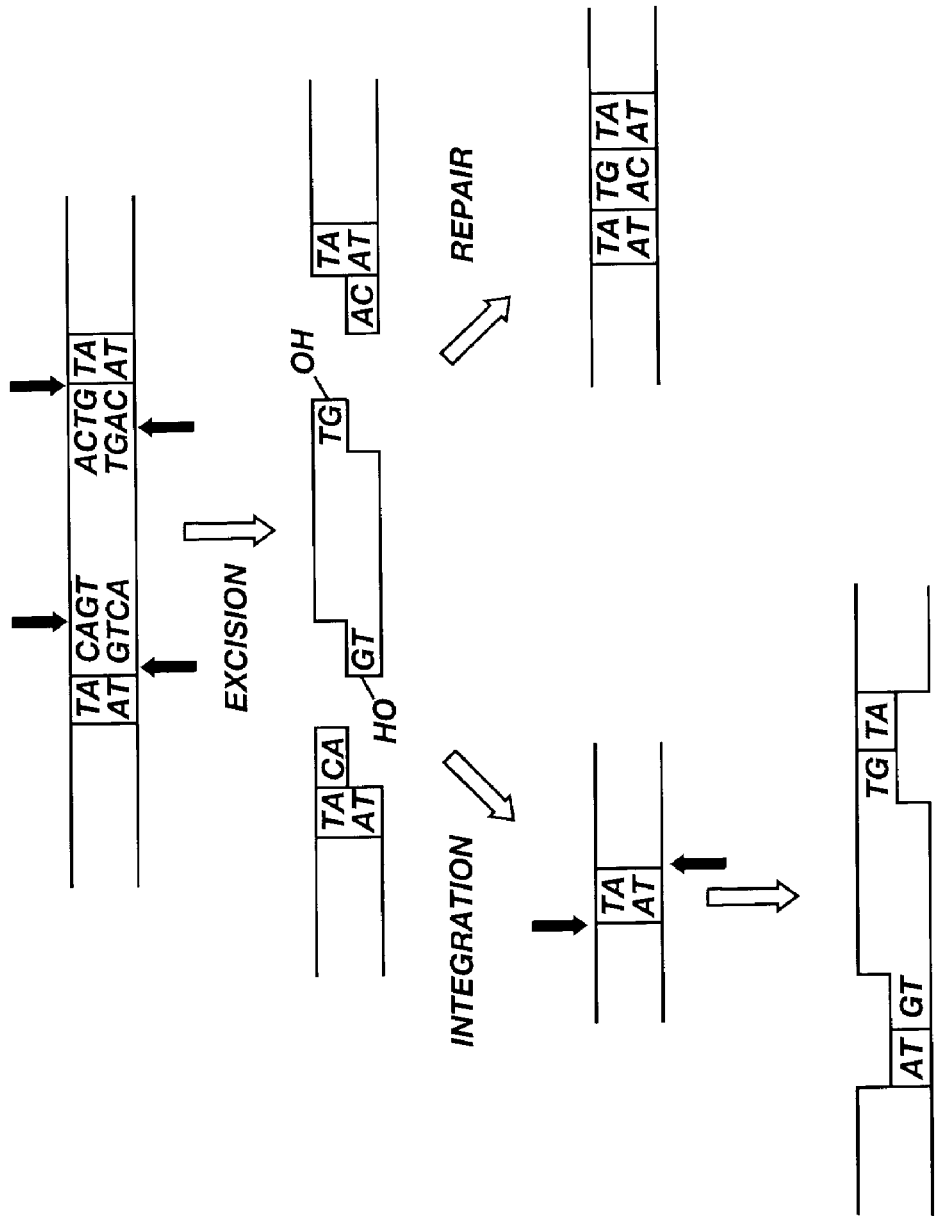
FIG. 7 depicts a model for Tc1 transposition. A model for non-replicative Tc1 transposition showing the excised, linear element with a 2 bp 3' staggered overhang. Integration results in a duplication of the TA target site. Repair of the double strand break leads to the generation of characteristic footprints (see also Van Luenen et al. 1994).

We have developed a cell-free Tc1 transposition system. Excision occurs by double strand breaks at the transposon ends resulting in 2 bp staggered 3' overhangs. A cut-and-paste mechanism of transposition appears to apply for Tc1 (FIG. 7). This mechanism was already proposed on the basis of genetic data (Plasterk 1991) as well as the analysis of in vivo transposition products (Van Luenen et al. 1994). Non-replicative transposition is shared with the bacterial transposon Tn7 (Bainton et al. 1991, 1993) and Tn10 (Bender and Kleckner 1986) as well as the Drosophila P element (Kaufman and Rio 1992). In contrast, the Mu and Tn3 tranposable elements transpose via a replicative mechanism (Grindley and Sherratt 1978; Shapiro 1979; Mizuuchi 1992). Tc1 transposition appears to be independent of addition of a nucleotide cofactor, whereas P elements use GTP (Kaufman and Rio 1992) and Tn7 uses ATP as cofactors (Bainton et al. 1993).

A striking feature of the Tc1/mariner family is the use of a TA dinucleotide as target site. An extensive study of target site choice in vivo had revealed the usage of only a subset of the available TA dinucleotides and a marked difference in target choice between the two related transposons Tc1 and Tc3 in *C. elegans* (Van Luenen and Plasterk 1994). We find the same overall integration pattern in vitro as had been observed in vivo. This suggests that the chromosomal context of the DNA does not affect target choice, at least in the region of the genome analyzed. Therefore, we favor the idea that the transposition complex primarily selects its target site on the basis of the primary DNA sequence flanking the TA, although a strong consensus sequence could not be identified (Van Luenen and Plasterk 1994). A clear influence of the chromatin structure has been demonstrated for retroviral integrations (Pryciak and Vannus 1992; Müller and Varmus 1994). These studies showed a preference for regions within nucleosomal DNA, probably due to the bending of the DNA. We cannot exclude that DNA binding proteins can affect regional preferences for Tc1 integration. Because nothing is known about the chromosomal organization of the gpa-2 gene, it will be of interest to compare integration sites using reconstituted nucleosomal DNA in vitro.

Transposition in vitro requires the extreme termini of the transposon containing the transposase binding site and the conserved hexanucleotide sequence, which is important for excision. We observe a decrease in transposition efficiency between transposition of a full-length transposon and the Tc1 element with only 26 bp terminal inverted repeats, which suggests that additional sequences can contribute to transposition efficiency. We have no indications for additional transposase binding sites, but perhaps small basic proteins like high mobility group proteins (Grosschedl et al. 1994) may bind and stimulate transposition. Alternatively, unique A-T-rich sequences found at the transposon ends may add a helping bend to the DNA. The conserved hexanucleotide sequence at the extreme termini of the transposon is shown to be important at least for the cleavage step. The 5' end single strand cleavage seen for one of the mutations (CA to TG) is perhaps an indication for a specific order of single strand cleavages, i.e., first the non-transferred strand, which would be the opposite of what has been reported for Tc10 (Bolland and Kleckner 1995).

Figure 8:
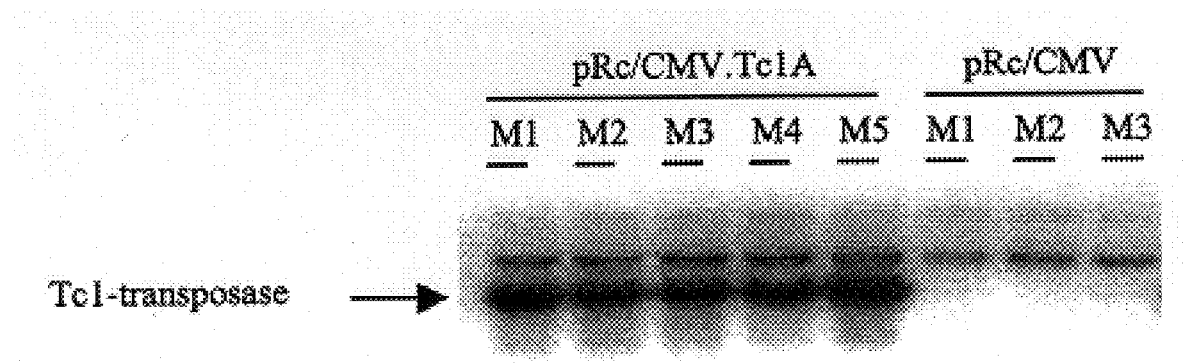
FIG. 8 Tc1-transposase is not toxic for human cells. The cell line 911 was transfected with 2 μg pRc/CMV.Tc1A or 2 μg pRc/CMV per 5 cm, and monoclonal cell lines were established from G418 resistant colonies. From each cell line, 50 μg whole cell extract was separated on a 10% PAA gel and subsequently analyzed for Tc1-transposase. Tc1-transposase was detected in the cell lines transfected with pRc/CMV.Tc1A (Lanes 1–5), whereas no Tc1-transposase could be detected in the negative control cell lines transfected with pRc/CMV (lanes 6–8).

Transposase purified from *E. coli* to near homogeneity is able to execute jumping of Tc1, which indicates that transposase is the only protein required for excision and integration of Tc1. The higher efficiency obtained with the nematode extract suggests that host factors may enhance the frequency of the reaction. It has, for instance, been shown that the mammalian proteins HMG1 and HMG2 can stimulate prokaryotic recombinations (Paull et al. 1993). The independence of species-specific factors might be the explanation why members of the Tc1/mariner family are dispersed over so many different phyla, possibly by means of horizontal transfer (Robertson and Lampe 1995). This is in contrast to P elements which are restricted to Drosophila species. Transposition of P elements in other species has not been observed (Rio et al. 1988). A possible candidate for a species-specific host factor in P transposition is the inverted repeat binding protein, IRBP (Beall et al. 1994). The simple cis- and trans-requirements for Tc1 transposition in vitro shows that this transposable element will be a good vector for gene delivery in a wide variety of animals. In order to determine the feasibility of the use of Tc1 transposons in human cells, we first tested whether the Tc1-transposase is toxic for human cells. The Tc1-transposase expression vector pRc/(CMV.Tc1A or the empty vector pRc/CMV (Invitrogen) was transfected into 911 cells; a human embryo retina cell line transformed by early region I of adenovirus type 5. Approximately 48 hours post-transfection, the cells were put on G418 selection medium. Stable cell lines derived from single colonies were established and screened for Tc1-transposase protein on a western blot (FIG. 8). All pRc/CMV.Tc1A transfected cell lines expressed Tc1-transposase, demonstrating that expression of Tc1-transposase is not toxic for human cells.

Figure 9:
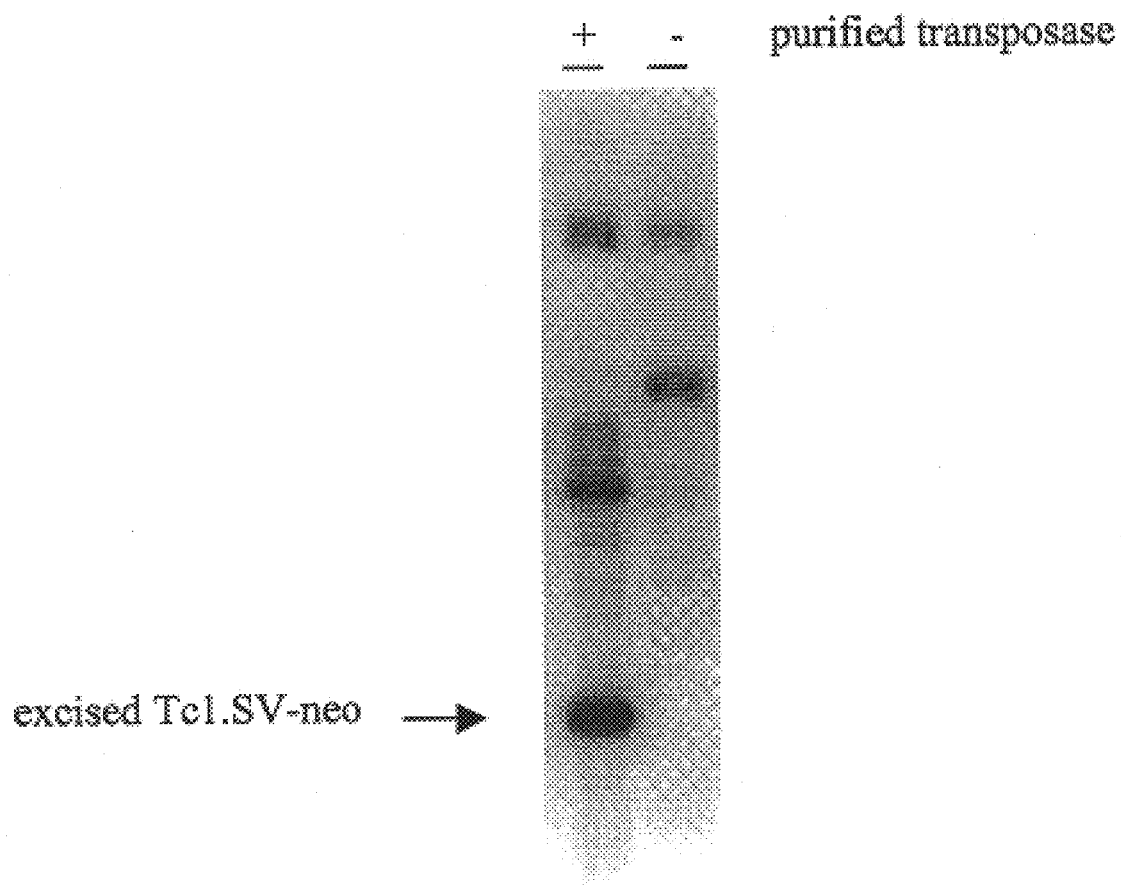
FIG. 9 is a Southern Blot of in vitro excision reaction products of pRP466.SV-neo1.PGK-tk2, catalyzed by Tc1-transposase purified from *E. coli*. Incubation of the donor plasmid pRP466.SV-neo1.PGK-tk2 with purified Tc1-transposase (Lane 1), but not with NEB (Lane 2) results in excision of the Tc1.SV-neo transposon (Lane 1). Thus, the plasmid pRP466.SV-neo1.PGK-tk2 can serve as a Tc1.SV-neo transposon donor plasmid.

Next, we examined whether Tc1-transposase supports transposition of a Tc1-derived transposon in human cells. To that end, the plasmid pRP466.SV-neo1.PGK-tk2 was constructed. This plasmid contains a neomycin resistance gene expression cassette under control of the SV40 promoter (SV-neo) flanked by the inverted repeats of Tc1 and an expression cassette for the Herpes Simplex Virus thymidine kinase under control of the phospho-glyceraldenhyde kinase promoter (PGK-tk) outside of the Tc1 inverted repeats. Excision of the SV-neo transposon from pRP466.SV-neo1.PGK-tk2 was tested in an in vitro excision assay using transposase purified from *E. coli*. Southern Blot analysis of the reaction products shows the appearance of excised 2.9 kb Tc1.SV-neo elements (FIG. 9). Thus, pRP466.SV-neo1.PGK-tk2 can serve as a Tc1.SV-neo transposon donor plasmid.

To determine whether transposition of Tc1 transposon-derived vectors occurs in human cells, the cell line 911 was transfected with the plasmid pRP466.SV-neo1.PGK-tk2, together with the Tc1-transposase expression vector pcDNA1/Tc1A or with the empty vector pcDNA1/amp (Invitrogen). Forty-eight hours post-transfection, the cells were put on G418 selection. After 18 days, G418 resistant colonies were counted (Table 2). Co-transfection of pcDNA1/Tc1A yielded approximately 40% more G418 resistant colonies, suggesting that, in addition to random integration, G418 resistant colonies were formed due to jumping of the Tc1-neo transposon into the cellular genome.

TABLE 2: Formation of G418 resistant colonies after co-transfection of pRP466.SV-neo1.PGK-tk2 with pcDNA1/Tc1A or pcDNA1/amp. The cell line 911 was co-transfected with pRP466.SV-neo1.PGK-tk2 and pcDNA1/Tc1A or pcDNA1/amp. For a period of 18 days, the transfected cells were put on G418 selection medium. Subsequently, the G418 resistant colonies were stained with methylene blue and counted. Co-transfection of pRP466.SV-neo1.PGK-tk2 with pcDNA1/Tc1A yielded approximately 40% more G418 resistant colonies than co-transfection with pcDNA1/amp. This indicates that, in addition to random integration, G418 resistant colonies were formed due to jumping of the Tc1-neo transposon into the cellular genome.

TABLE 2

| Transfected DNA/5 cm dish | n = | mean number of colonies |
|---|---|---|
| 2 μg pcDNA1/Tc1A + 0.1 μg pRP466.SV-neo1.PGK-tk2 | 3 | 51 |
| 2 μg pcDNA1/amp + 0.1 μg pRP466.SV-neo1.PGK-tk2 | 3 | 37 |
| 2 μg pcDNA1/Tc1A + 0.5 μg pRP466.SV-neo1.PGK-tk2 | 2 | 206 |
| 2 μg pcDNA1/amp + 0.5 μg pRP466.SV-neo1.PGK-tk2 | 2 | 144 |
| 2 μg pcDNA1/Tc1A + 2 μg pRP466.SV-neo1.PGK-tk2 | 2 | 342 |
| 2 μg pcDNA1/amp + 2 μg pRP466.SV-neo1.PGK-tk2 | 2 | 251 |
| no DNA | 2 | 0 |

The presence of the PGK-tk expression cassette on the plasmid pRP466.SV-neo1.PGK-tk2 outside of the Tc1 inverted repeats allowed us to discriminate between plasmid integration and transposition of the Tc1.SV-neo transposon. Thymidine kinase phosphorylates the anti-viral prodrug Ganciclovir (GCV), after which it acts as a chain terminator of DNA synthesis, thereby killing the tk expressing cells. When plasmid integration occurs, in most cases both the SV-neo and PGK-tk expression cassetts are integrated into the 911 genome, rendering the cell lines G418 resistant and GCV sensitive. When transposition of the SV-neo transposon takes place, however, the cell lines will be G418 resistant and GCV insensitive, because the PGK-tk expression cassette is not integrated into the host cell genome. In total, 73 independent G418 resistant cell lines were established from the above mentioned transfection, and screened for GCV. Table 3 shows that co-transfection of pRP466.SV-neo1.PGK-tk2 with PCDNA1/Tc1A resulted in the formation of more tk-negative cell lines (64–77%) than co-transfection with pcDNA1/amp (32–44%).

TABLE 3: Expression of HSV-tk in G418 resistant cell lines co-transfected with pRP466.SV-neo1.PGK-tk2 with pcDNA1/Tc1A or pcDNA1/amp. Co-transfection of pRP466.SV-neo1.PGK-tk2 with pcDNA1/Tc1A yielded more HSV-tk negative (Gangiclovir resistant) colonies than co-transfection with pcDNA1/amp.

TABLE 3

| Transfected DNA | n = | % HSV-tk negative |
| --- | --- | --- |
| 2 µg pcDNA1/Tc1A + 0.1 µg pRP466.SV-neo1.PGK-tk2 | 16 | 77 |
| 2 µg pcDNA1/Tc1A + 0.5 µg pRP466.SV-neo1.PGK-tk2 | 19 | 64 |
| 2 µg pcDNA1/amp + 0.1 µg pRP466.SV-neo1.PGK-tk2 | 19 | 32 |
| 2 µg pcDNA1/amp + 0.5 µg pRP466.SV-neo1.PGK-tk2 | 18 | 44 |

Random integration of circular plasmid DNA first requires linearization of the DNA due to a double strand DNA break before integration into the host genome can occur. The PGK-tk expression cassette covers approximately ⅓ of the total of the plasmid DNA (excluding the neomycin SV-neo expression cassette for which the cell lines were selected). If this process is assumed random and if a single copy of the plasmid integrates, one would expect around 33% of the DNA breaks to occur in the PGK-tk expression cassette, thereby abolishing tk expression. Therefore, the percentage of tk negative cell lines that were generated by co-transfection of pRP466.SV-neo1.PGK-tk2 and pcDNA1/amp was within expectation. The higher incidence of GCV resistant clones after co-transfection of pRP466.SV-neo1.PGK-tk2 with pcDNA1/Tc1A again strongly suggests that the Tc1.SV-neo transposon jumped from the pRP466.SV-neo1.PGK-tk2 into the human genome.

The most direct way to discriminate between plasmid integration and transposition events is sequencing the DNA that flanks the transposon that is integrated into the host cell genome. After plasmid integration, the surrounding DNA sequences will be identical to the sequences flanking the transposon in the plasmid pRP466.SV-neo1.PGK-tk2. After transposition, the surrounding sequences will be of human genomic origin, and thus be different form those in the plasmid pRP466.SV-neo1.PGK-tk2. Genomic DNA from independent tk-minus/G418-resistant colonies was isolated and digested with Sau3A. To the genomic fragments, an oligo-cassette ("vectorette") was ligated. The vectorette consists of two oligonucloeotides which have complementary sequences at their ends but are not complementary in the middle. Fragments that contain transposon and flanking sequences are amplified in a PCR using an oligo complementary to the transposon end and pointing to the flanking sequence in combination with an oligo that is complementary to the middle of the vectorette sequence. PCR products were analyzed on an agarose gel and the amplified DNA Fragments were sequenced. Thus far, in two out of five cases we found that the transposon was present, flanked by a TA dinucleotide and followed by a new sequence. These integrations represent genuine transposon events showing that Tc1 can jump in human cells when Tc1-transposase is provided.

MATERIALS AND METHODS

Plasmid Constructions pRP466 contains a Tc1 element with 0.4 kb flanking sequences derived from P1M40 (Mori 1988) cloned as a BamHI-XbaI fragment into pUC19, pRP467 and pRP468 are derivatives of pRP466 in which either a ClaI-Asp718 or PstI-ApaI fragment is deleted. pRP472 is a pACB104 (Boyd and Sherratt 1995) derivative which contains Tc1 with the AvaI-HindII fragment of pBR322 inserted between the ClaI and ApaI sites. Cloning of the XbaI-BamHI fragment of pRP466 with the HindII $Kan^R$-cassette of pUC4k (Poharmacia) between the XhoI-sites into pACB 104 resulted in pRP490. pRP491 is comparable to pRP490; all the internal Tc1 sequences have been replaced except the terminal 26 bp.

The plasmid pRP466.SV-neo1.PGK-tk2 was constructed as follows: pRP466 was digested with XhoI and blunted with Klenow and dNTPs. The plasmid pRc/CMV (Invitrogen) was digested with BamHI and EcoRI and blunted with Klenow and dNTPs. Subsequently, the BamHI/EcoRI SV-neo fragment was cloned into XhoI digested pRP466, giving rise to pRP466.SV-neo1. The plasmid pRP466.SV-neo1 was digested with EcoRI and blunted with Klenow and dNTPs. The plasmid pPGK-tk (PCT/NL/00195) was digested with PvuII. The PvuII PGK-tk fragment was cloned into EcoRI digested pRP466.sv-neo1, giving rise to pRP466.SV-neo1.PGK-tk2.

The plasmid pRc/CMV.Tc1A contains the Tc1-transposase cDNA, which was amplified from pRP470 (Vos et al., 1993) with the primers 5'-CCCCAAGCTTGCCACCATGGTAAAATCTGTT-GGGTGTAAAAATC (SEQ ID NO: 1) and 5'-GCTCTAGATGCTTAATACTTTGTCGCGTATCC (SEQ ID NO: 2) using eLONGase according to standard protocol of the supplier (Gibco BRL). PCR was performed on a Biometra TRIO THERMABLOCK, Amplification program: 94° C. for 1 minute, 1 cycle, 94° C. for 30 seconds +−52° C. for 30 seconds +68° C. for 1 minute, 35 cycles; 68° C. for 1 minute. The PCR fragment was digested with HindIII/XbaI and cloned into HindIII/XbaI digested pRc/CMV, giving rise to pRc/CMV.Tc1A. The integrity of the Tc1A cDNA was confirmed by sequencing. The pRc/CMV plasmid contains a neomycin resistance gene expression cassette. The plasmid pcDNA1/Tc1A contains the HindIII/XbaI Tc1A fragment of pRc/CMV.Tc1A cloned into HindIII/XbaI digested pcDNA1/amp (Invitrogen). The pcDNA1/amp plasmid does not contain a neomycin resistance gene expression cassette. All restriction enzymes, primers, Klenow and dNTPs were purchased from Gibco BRL.

Southern Blotting

For FIG. 9: The product of the in vitro excision reaction was separated on a 0.8% agarose 0.5×TBE gel by electrophoresis for five hours at 70 Volts. Subsequently, the gel was rinsed in Southern Blot buffer (o0.4 M NaOH, 0.6 M NaCl) for 30 minutes and the DNA was blotted overnight onto HYBOND-N⁺ (Amersham). After blotting, the gel was rinsed in 5×SSPE and pre-hybridized for three hours in 50% formamide, 5×Denhardts, 5×SSPE, 5% dextrane sulphate, 1% SDS and 200 µg/ml haring sperm DNA and overnight hybridized with a randomly primed $^{32}$P-labelled (RTS radprime DNA labeling system, Gibco BRL) neo probe (NcoI fragment of pPGK-tk) at 42° C. Subsequently, the blot was extensively washed in 5×6SPE/0.1% SDS at 65° C. The blot was exposed to HyperFilm (Amersham) at room temperature.

Western Blotting

Cells were washed twice with PBS (NPBI) and lysed and scraped in RIPA (1% NP-40, 0.5% sodium deoxycholate and 0.1% SDS in PBS, supplemented 1 mM phenylmethylsulfonylfluoride and 0.1 mg/ml trypsin inhibitor). After 15 minutes incubation on ice, the lysates were cleared by centrifugation. Protein concentrations were determined by the Bio-Rad protein assay, according to standard procedures of the supplier (BioRad). Whole-cell extracts were fractionated by SDS-PAGE on 10% gels. Proteins were transferred onto IMMOBILON P membranes (Millipore) and incubated with an Tc1 transposase antibody (Schukkink et al., 1990). The secondary antibody is a horseradish-peroxidase conjugated goat anti rabbit antibody (Bio Rad). The antibody complexes were visualized with the ECL detection system according to the manufacturer's protocol (Amersham).

Cell Culture and Transfection

The cell line 911 (Fallaux et al., 1996) was cultured in Dulbecco's modified Eagles medium (Gibco BRL) supplemented with 10% FBS (Gibco BRL) at 37° C. and 5% $CO_2$. Selection of the transfected cells with G418 (Gibco BRL) vias performed at a concentration of 500 µg/ml. Selection with Ganciclovir (Roche) was performed at a concentration of 10 µg/ml. DNA was transfected into 911 cells using the Calcium Phosphate Transfection System, according to the manufacturer's protocol (Gibco BRL). Briefly, one day prior to transfection, 911 cells were plated at 30% density on 5 cm tissue culture dishes (Greiner). The next day, cells were incubated with calcium phosphate precipitated DNA for 15 hours. Subsequently, the cells were washed twice with PBS and fresh medium was added. Approximately 48 hours post-transfection cells were put on G418 selection medium. G418 resistant colonies appeared around day 6. Single colonies were picked and cell lines were established.

Sequencing of the Transposon Flanks 100 ng genomic DNA was digested in 20 µl using 4 units Sau3A (Boehringer Mannheim) according to instructions of the supplier. After 2 hours at 37° C., the enzyme was inactivated by incubating 15 minutes at 65° C. Equimolar amounts of the vectorette oligo's (503: 5'-GATCCAAGGAGAGGACGCTGTCTGTCGAAGGT-AAGGAACGGA CGAGAGAAGGGAGA (SEQ ID NO: 3) and 504:5'-TCTCCCTTCTCGAATCGTAA CCGTTCGTACGAGAATCGCTGTCCTCTCCTTG) (SEQ ID NO: 4) were mixed in the presence of 10 mM Tris-HCl pH7.5 and 1 mM EDTA. The mixture was heated to 80° C. and allowed to cool down to 40° C. The final concentration of the vectorette-oligo-cassette is 10 pmol/µl. 15 pmoles of the vectorette were overnight ligated at 16° C. to the digested DNA in a 100 µl volume using 5 units ligase (Boehringer Mannheim) according to the instructions of the supplier. In the first PCR, 3 µl of the DNA is used in a volume of 25 µl using 1 unit Taq polymerase (Gibco BRL) according to the instructions of the supplier. The final concentration of the oligo's is 0.4 pmoles. The PCR consisted of 30 cycles with 1 minuted at 95° C., 1 minute at 58° C. and 1 minute at 72° C. To increase the specificity and the sensitivity, a second PCR with nested primers was performed using 0.01 µl template from the first PCR. The conditions of the PCR were identical to the first PCR. The oligo's used were Tc1L2 (5'-TCAAGTCAAATGGATGCTTGAG) (SEQ ID NO: 5) or Tc1R2 (5'-GATTTTGTGAACACTGTGGTGAAG) (SEQ ID NO: 6) and 337new (5'-GTACGAGAATCGCTGTCCTC) (SEQ ID NO: 7). The PCR products were analyzed on a 1% agarose gel. Amplified DNA fragments were excised from gel and DNA was extracted using the QIAEX II gel extraction kit (Qiagen). The DNA was taken up in 20 µl water after isolation from gel. The transposon primer Tc1L2 or Tc1R2was radiolabeled using $^{32}$P-ATP and polynucleotide kinase (Boehringer Mannheim) according to the instructions of the supplier. Using 0.25 pmoles of radiolabeled primer and the isolated DNA, a PCR was performed using 0.5 units Taq polymerase (Gibco BRL) and one of the ddNTP mixtures (containing either ddATP (160 µM ddATP and 5 µM of each dNTP in 10 mM Tris-HCl pH 8, 1 mM EDTA), ddTTP (250 µM ddTTP and 5 µM of each dNTP in 10 mM Tris-HCl pH 8, 1 mM EDTA), ddGTP (32 µM ddGTP and 5 µM of each dNTP in 10 mM Tris-HCl pH 8, 1 mM EDTA) or ddCTP (160 µM ddCTP and 5 µM of each dNTP in 10 mM Tris-HCl pH 8, 1 mM EDTA)). The final volume was 20 µl. 20 cycles were performed with 1 minute at 95° C.; 1 minute 58° C.; 1 minute 72° C. The samples were analyzed on a 6% denaturing polyacrylamide gel in 1×TBE.

Transgenesis of C. elegans

A transgenic Bristol line was obtained after microinjection (Mello et al. 1991) of 150 mg/ml pRP469 and 5 mg/ml pRP465 (Vos et al. 1993), 50 mg/ml pRF4 (Kramer et al. 1990) in strain CB1392 (nuc-1 9e1392)). A stable line, NL818 (pkls221), was generated by x-ray irradiation (Way et al. 1991).

Extract Preparation

Stable line NL818 was grown in liquid culture at 18° C. and heat shocked for 3 hours at 33° C. to induce transposase expression. After 2 hours of further growth at 18° C., nuclear extracts were prepared as described (Vos et al. 1993) with differences in the buffers. NIB: 25 mM Tris pH 7.5, 20 mM KCl, 0.5 M sucrose, 0.5 mM EDTA, 5 mM b-mercaptoethanol, 0.1 mM PMSF, NEB: 25 mM Tris pH 7.5, 0.1 mM EDTA, 500 mM NaCl, 15% glycerol, 0.25% TWEEN-20, 0.1 mM PMSF, 1 mM DTT. Nuclear extact contains 2.5 mg/ml protein; concentration of Tc1A is about 10 mg/ml.

Recombinant Transposase Expression and Purification

E. coli strain BL21 pLysS was transformed with pRP470 containing the Tc1 transposase gene under the control of a T7 promoter (Vos et al. 1993), grown in 2xYT medium and induced at an OD of 0.6 at 600 nm with 0.5 mM IPTG for 3 hours at 37° C. Inclusion bodies were puriufied as described by Nagai and Thogersen (1978). Inclusion bodies were dissolved in 8 M urea, 20 mM Na-phosphate pH 6.0 and loaded on a CM cellulose CL-6B column (Pharmacia). The protein was elated with a linear gradient from 0 to 500 mM NaCl. The transposase containing fraction was loaded on a SEPHACRYL S400 HR gel filtration column equilibrated in 6 M guanidiumhydrochloride, 50 MM Tris pH 8.0. Transposase fractions were dialysized against 8 M urea, 50 mM Tris pH 8.0, 1 mM DTT. The protein was loaded on an S SEPHAROSE FF column and euted with 500 mM NaCl in the same buffer. All steps were performed at room temprature. The protein was renatured by a 100×dilution into ice-cold buffer: 50 mM Tris pH 8.0, 100 mM NaCl, 5 mM DTT, 5 mM $MgCl_2$. After 30 minutes, insoluble protein was removed by centrifugation for 15 minutes in an Eppendorf centrifuge. Transposase concentration was 200 mg/ml and estimated to be more than 90% pure.

In Vitro Transposition Reactions

Standard reaction conditions: 25 mM Tris pH 8.0, 25 mM NaCl, 1 mM DTT, 10% ethylene glycol, 5 mM $MgCl_2$ (or 2.5 mM EDTA), 4 mM spermidine, 0.05 mg/ml BSA. 200 ng of donor plasmid was preincubated with 2.5 ml worm extract or 0.25 ml of purified protein for 5 minutes on ice before addition of 2.5 mg target DNA in a total volume of 50 ml. Incubation was for 1 hour at 30° C. Reactions were stopped by addition of 5.5 ml of 250 mM Tris pH 8.0, 50 mM EDTA, 5% SDS. 2 mg/ml proteinase K. After 1 hour at 37° C., the DNA was precipitated and resuspended in 50 ml water.

Mapping of In Vitro Cleavage Sites

Linear PCR amplification was in 20 ml using a 5 ml template and 0.5 pmol primer for 20 cycles; 1' at 94° C., 1' at 60° C., 1' at 72° C., essentially as described (Craxton 1991). Sequence primers: BIGR=5'-AGATTTCCACTTATATCATGTTTTATGTTTTGC (SEQ ID NO: 8), R2 (Van Luenen and Plasterk 1994).

Genetic Assay

Electrocompetent DS941 lambda lysogen (Flinn et al. 1989) bacteria were prepared and used as described (Zabarovsky and Winberg 1990). The donor plasmid contains a lambda origin of replication and cannot replicate in the DS941 lambda lysogen; the target plasmid has Col E1 origin of replication. One to 5 ml of DNA was used per electrophoration and 5% of the bacteria were, after dilution, plated on ampicillin. The remaining bacteria were plated on double selection. This yielded, depending on the efficiency, up to 200 transformants.

REFERENCES

Bainton, R. J., P. Gamas, and N. L. Craig, 1991. Tn7 transposition in vitro proceeds through an excised transposon intermediate generated by staggered breaks in dDNA. *Cell* 65: 805–816.

Bainton, R. J., K. M. kubo, J.-n. Feng, and N. L. Craig, 1993. Tn7 transposition: target DNA recognition is mediated by multiple Tn7-encoded proteins in a purified in vitro system. *Cell* 72: 931–943.

Beall, D. L., A. Admon, and D. C. Rio, 1994. A Drosophila protein homologous to the human p70 Ku autoimmune antigen interacts with the P transposable element, inverted repeats. *Proc. Natl. Acad. Sci.* USA 91: 12681–12685.

Bender, J. and N. Kleckner, 1986. Genetic evidence that Tn10 transposes by a nonreplicative mechanism. *Cell* 45: 801–815.

Bolland, S. and N. Kleckner, 1995. The two single-strand cleavages at each end of Tn10 occur in a specific order during transposition. *Proc. Natl. Acad. Sci.* USA 92: 7814–7818.

Boyd, A./C. And D. J. Sherratt, 1995. The pCLIP plasmids: versatile cloning vectors based on the bacteriophage lambda origin of replication. *Gene* 153: 57–62.

Clar, J. M. 1988, Novel non-templated nucleotide addition catalyzed by procaryotic and eukaryotic DNA polymerases. *Nucleic Acids Res.* 16: 9677–9686.

Collins, J., B. Saari, and P. Anderson, 1987. Activation of a transposable element in the germ line but not the soma of *Caenorhabditis elegans*. *Nature* 328: 726–728.

Craxton, M., 1991. Linear amplification sequencing, a power method for sequencing DNA. METHODS: A companion to Meth. Enzymol, 3: 20–26.

Doak, T. G., F. P. Doerder, C. L. Jahn, and G. Herrick, 1994. A proposed superfamily of transposase-related genes: new members in transposon-like elements of ciliated protozoa and a common "D35E" motif. *Proc. Natl. Acad Sci.* USA 91: 942–946.

Emmons, S. W., L. Yenner, K. S. Ruan, and D. Katzenberg, 1983. Evidence for a transposon in *Caenorhabditis elegans*. *Cell* 32: 55–65.

Fallaux, F. J., Kranenburg, O., Cramer, S. J., Houweling, A., van Ormondt, H., Hoeben, R. C. and van der Eb, A. J. 1996. Characterization of 911: A new helper cell line for the titration and propagation of early region-1 deleted adonoviral vectors. *Human Gene Therapy* 7: 215–222.

Flinn, H. L., M. Burke, C. J. Stirling and D. J. Sherratt, 1989. Use of gene replacement to construct *Escherichia coli* strains carrying mutations in 2 genes required for stability of multicopy plasmids. *J. Bacteriol.* 171: 2241–2243.

Grimdley, N. D. F. and D. J. Sherratt, 1978. Sequence analysis of IS1 insertion sites: models for transposition. *Cold Spring Harbor Symp. Quart. Biol.* 45: 125–133.

Grosschedl, R., K. Giese, and J. Pagel, 1994. HMG domain proteins: architectural elements in the assembly of nucleoprotein structures. *Trends Genet.* 10: 94–100.

Henikoff, S., 1992. Detection of *Caenorhabditis transposon* homologs in diverse organisms. *New Biol.* 4: 382–388.

Kaufman, P. D., and D. C. Rio, 1992. P element transposition in vitro proceeds by a cut-and-paste mechanism and uses GTP as cofactor. *Cell* 69: 27–39.

Kramer, J. M., R. P. French, E. Park, and J. J. Johnson, 1990. The *Caenorhabditis elegans* rol-6 gene, which interacts with the sqt-1 collagen gene to determine organismal morphology, encodes a collagen, *Moll. Cel. Biol.* 10: 2081–2089.

Loukeris, T. G., Livadaras, I., Arca, B., Zabalou, S., Savakis, C., 1995. Gene transfer into the medfly, *Ceratitis capitata*, with a *Drosophila hydei* transposable element *Science*, 270 (5244): 2002–5.

Mello, C. C., J. M. Kramer, D. Stinchcomb, and V. Ambros, 1991. Efficient gene transfer in *C. elegans*: extrachromosomal maintenance and integration of transforming sequences. *EMBO J.* 10: 3959–3970.

Mizuuchi, K. 1992. Transpositional recombination: mechanistic insights from studies of Mu and other elements. *Annu. Rev. Biochem.* 61: 1011–1051.

Mori, I, 1988. "Analysis of gernline transposition and excision of Tc1 transposable elements in *Caenorhabditis elegans*." Ph. D. thesis, Washington University, St Louis, Mo.

Müller, H.-P. And H. E. Varmus, 1994. DNA bending create favored sites for retroviral integration: an explanation for preferred insertion sites in nucleosomes. *EMBO J.* 13: 4704–4714.

Nagai, K. and H. C. Thogersen, 1987. Synthesis and sequence-specific proteolysis of hybrid proteins produced in *Eschericia coli*. *Methods Enzymol.* 153: 461–481.

Paull, T. T., M. J. Haykinson, and R. C. Johnson 1993. The nonspecific DNA-binding and -bending proteins HMG1 and HMG2 promote the assembly of complex nucleoprotein structures. *Genes & Dev.* 7: 1521–1534.

Plasterk, K. H. A. 1991. The origin of footprints of the Tc1 transposon of *Caenorhabditis elegans. EMBO J.* 10: 1919–1925.

Plasterk, R. H. A. 1995. The Tc1/mariner transposon family *In Transposble Elements* (eds. H. Seadler and A. Gierl), Springer Verlag, Heidelberg.

Pryciak, P. M. and H. E. Varmus, 1992. Nucleosomes, DNA-binding proteins, and DNA sequence modulate retroviral integration target site selection. *Cell* 69: 769–780.

Radice, A. D., B. Bugaj, D. H. A. Fitch, and S. W. Emmons, 1994. Widespread occurrence of the Tc1 transposon family: Tc1-like transposons from teleost fish. *Mol. Gen. Genet.* 244: 606–612.

Rio, D. C., G. Barnes, F. A. Laski, J. Rine, and G. M. Rubin. 1988. Evidence for Drosophila P element transposase activity in mamalian cells and yeast *J. Mol. Biol.* 200: 411–415.

Robertson, H. M. 1995. The Tc1-mariner superfamily of tansposons in animals. *J. Insect. Physiol.* 41: 99–105.

Robertson, H. M. 1993. The mariner transposable element is widespread in insects. *Nature* 362: 241–245.

Robertson, H. M. and D. J. Lmape, 1995. Recent horizontal transfer of a mariner transposable element among and between Diptera and Neuroptera. *Mol. Bol. Evol.* 12: 850–862.

Rosenzweig, B., L. W. Liao, and D. Hirsch, 1983. Sequence of the *C. elegans* transposable element Tc1. *Nucleic Acids Res.* 12: 4201–4209.

Schukkink, R. F. and Plasterk, R. H. A. 1990. TcA, the putative transposase of the *C. elegans* Tc1 transposon, has an N-terminal DNA binding domain. Nucleic Acids Research 18: 895–900.

Shapiro, J. A. 1979. Molecular model for the transposition and replication of bacteriophage Mu and other transposable elements. *Proc. Natl. Acad. Sci.* USA 76: 1933–1937.

Van Luenen, H. G. A. M. and R. H. A. Plasterk, 1994. Target site choice of the related transposable elements Tc1 and Tc3 of *Caenorhabditis elegans. Nucleic Acids Res.* 22: 262–269.

Van Luenen, H. G. A. M. van Luenen, and R. H. A. Palasterk 1993. Characterization of the *Caenorhabditis elegans* Tc1 tansposase in vivo and in vitro. *Genes & Dev.* 7: 1244–1253.

Vos, J. C. and R. H. A. Plasterk 1994. Tc1 transposase of *Caenorhabditis elegans* is an endonuclease with a bipartite DNA binding domain. *EMBO J.* 13: 6125–6132.

Way, J. C., L. Wang, J.-O. Run, and A. Wang 1991. The mec-3 gene contains cis-acting elements mediating positive and negative regulation in cells produced by asymmetric cell division in *Caenorhabditis elegans. Genes & Dev.* 5: 2199–2211.

Zabarosky, E. R. and G. Winberg 1990. High efficiency electrophoration of ligated DNA into bacteria. *Nucleic Acids Res.* 18: 5912.

---

What is claimed is:

1. A vector for integrating additional nucleic acid material into a cell of a certain genome of a first genus, said vector comprising:
two Tc1/mariner transposase binding sites and a cut site corresponding to each of said Tc1/mariner superfamily transposase binding sites,
wherein said Tc1/mariner transposase binding sites are from a Tc1/mariner transposon found in a second genus;
wherein each of said Tc1/mariner transposase binding sites are in close proximity to said corresponding cut site; and
wherein the additional nucleic acid material is integrated between said two Tc1/mariner transposase binding sites of the vector.

2. A vector according to claim 1 wherein said transposase binding sites and said cut sites are corresponding sites in transposons from the Tc1/mariner superfamily of transposons.

3. A vector according to claim 1 wherein said Tc1/mariner transposase binding sites and said cut sites are Tc1/mariner transposons.

4. A vector according to claim 1 wherein at least one of said transposase binding sites further comprises at least terminal 26 base pairs of a Tc1/mariner transposase binding site and wherein at least one of said cut sites in a Tc1/mariner transposase cut site.

5. A vector according to claim 1 which transduces a target cell.

6. A vector according to claim 1 further comprising a nucleic acid sequence which encodes transposase activity, wherein said transposase activity is functional for said Tc1/mariner transposase binding sites and said cut sites.

7. A vector according to claim 1 wherein at least a portion of said additional nucleic acid material encodes a protein.

8. A vector according to claim 1 wherein said additional nucleic acid material encodes a transcription-blocking nucleic acid.

9. A method for integrating additional nucleic acid material into a target cell's genome, said method comprising:
transducing the target cell with a vector comprising
two Tc1/mariner transposase binding sites and
a cut site corresponding to each of said Tc1/mariner superfamily transposase binding sites,
wherein said Tc1/mariner transposase binding sites are from a Tc1/mariner transposon found in a second genus and
said Tc1/mariner transposase binding sites ire in close proximity to said corresponding cut site for said Tc1/mariner transposase; and
wherein the additional nucleic acid material is integrated between said two Tc1/mariner transposase binding sites of the vector; and
providing the target cell with Tc1/mariner transposase activity, wherein said Tc1/mariner transposase activity is functional for said Tc1/mariner transposase binding sites and said cut sites of said vector.

10. A method according to claim 9 wherein said transposase binding sites are selected from Tc1/mariner superfamily transposase binding sites and wherein said cut sites are selected from Tc1/mariner superfamily transposase cut sites.

11. A method according to claim 9 wherein said vector transduces a target cell.

12. A method according to claim 9 wherein said vector is a viral vector.

13. A method according to claim 12 wherein said viral vector is selected from the group consisting of adenoviral, retroviral, and adeno-associated viral vectors, and wherein said transduction step further comprises utilization of said viral vector.

14. A recombined target cell having nucleic acid material, said cell comprising:
a target cell genome and
additional nucleic acid material integrated into said target cell genome,
wherein said additional nucleic acid material is integrated into said target cell genome by
transducing the target cell with a vector comprising
two Tc1/mariner transposase binding sites and
a cut site corresponding to each of said Tc1/mariner superfamily transposase binding sites,
wherein said Tc1/mariner transposase binding sites comprise a Tc1/mariner transposon found in a second genus;
wherein each of said Tc1/mariner transposase binding sites are in close proximity to said corresponding cut site for said Tc1/mariner transposase; and
wherein the additional nucleic acid material is integrated between said two Tc1/mariner transposase binding sites of the vector; and
providing the target cell with Tc1/mariner transposase activity, wherein said Tc1/mariner transposase activity is functional for said Tc1/mariner transposase binding sites and said cut sites of said vector.

15. The recombined target cell of claim 14, wherein said Tc1/mariner transposase binding sites are selected from the group consisting of Tc1/mariner superfamily transposase binding sites and wherein said cut sites are selected from the group consisting of Tc1/mariner superfamily transposase cut sites.

16. The recombined target cell of claim 15 wherein said additional nucleic acid material encodes a protein.

17. The recombined target cell of claim 15 wherein said vector comprises a viral vector.

18. The recombined target cell of claim 17 wherein said viral vector is selected from the group consisting of adenoviral, retroviral, and adeno-associated viral vectors, and wherein said transduction step further comprises utilization of said viral vector.

19. A method of integrating a nucleic acid of interest into nucleic acid material of a first genus, said method comprising:

providing a functional Tc1/mariner transposon of a second genus; and transducing the nucleic acid material of the first genus using said functional Tc1/mariner transposon of the second genus.

* * * * *